US008152748B2

(12) United States Patent
Randolph

(10) Patent No.: US 8,152,748 B2
(45) Date of Patent: Apr. 10, 2012

(54) OFFLOADING AND REDUCED-PRESSURE TREATMENT SYSTEMS AND METHODS

(75) Inventor: Larry Tab Randolph, San Antonio, TX (US)

(73) Assignee: KCI Licensing, Inc., San Antonio, TX (US)

(*) Notice: Subject to any disclaimer, the term of this patent is extended or adjusted under 35 U.S.C. 154(b) by 432 days.

(21) Appl. No.: 12/404,020

(22) Filed: Mar. 13, 2009

(65) Prior Publication Data
US 2009/0234264 A1 Sep. 17, 2009

Related U.S. Application Data

(60) Provisional application No. 61/036,433, filed on Mar. 13, 2008.

(51) Int. Cl.
*A61F 13/00* (2006.01)
(52) U.S. Cl. .......... 602/61; 602/42; 602/46; 602/66; 604/289; 604/290
(58) Field of Classification Search .......... 602/2, 54, 602/60–66; 604/289, 290; 36/140, 43
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |

(Continued)

FOREIGN PATENT DOCUMENTS

AU 550575 A1 8/1982

(Continued)

OTHER PUBLICATIONS

N.A. Bagautdinov, "Variant of External Vacuum Aspiration in the Treatment of Purulent Diseases of the Soft Tissues," *Current Problems in Modem Clinical Surgery: Interdepartmental Collection*, edited by V. Ye Volkov et al. (Chuvashia State University, Cheboksary, U.S.S.R. 1986);pp. 94-96.

(Continued)

*Primary Examiner* — Kim M Lewis
(74) *Attorney, Agent, or Firm* — SNR Denton US LLP

(57) ABSTRACT

An offloading and reduced-pressure treatment system includes an offloading and reduced-pressure treatment device, which has a plantar member formed from an offloading manifold material. The offloading and reduced-pressure treatment system further includes a reduced-pressure interface fluidly coupled to the pressure-transmitting layer of the plantar member, a reduced-pressure source, and a reduced-pressure delivery conduit fluidly coupled to the reduced-pressure source and to the offloading and reduced-pressure treatment device. The offloading manifold material includes a first barrier layer, a support layer, a pressure-transmitting layer and a second barrier layer. The offloading and reduced-pressure treatment device may also have a dorsal member and a bridge member. Methods are also presented.

32 Claims, 7 Drawing Sheets

U.S. PATENT DOCUMENTS

| | | | |
|---|---|---|---|
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,000,164 A | 3/1991 | Cooper |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,688,225 A | 11/1997 | Walker |
| 5,761,834 A | 6/1998 | Grim et al. |
| 5,784,811 A | 7/1998 | Mauch |
| 5,809,665 A | 9/1998 | Suenaga |
| 5,864,969 A | 2/1999 | Mauch |
| 5,913,838 A | 6/1999 | Reilly |
| 6,071,267 A | 6/2000 | Zamierowski |
| 6,129,692 A | 10/2000 | Mathis |
| 6,135,116 A | 10/2000 | Vogel et al. |
| 6,178,662 B1 | 1/2001 | Legatzke |
| 6,241,747 B1 | 6/2001 | Ruff |
| 6,287,316 B1 | 9/2001 | Agarwal et al. |
| 6,345,623 B1 | 2/2002 | Heaton et al. |
| 6,360,457 B1 | 3/2002 | Qui et al. |
| 6,361,512 B1 | 3/2002 | Mackay et al. |
| 6,425,194 B1 | 7/2002 | Brie |
| 6,488,643 B1 | 12/2002 | Tumey et al. |
| 6,493,568 B1 | 12/2002 | Bell et al. |
| 6,553,998 B2 | 4/2003 | Heaton et al. |
| 6,631,568 B2 | 10/2003 | Howlett et al. |
| 6,736,787 B1 | 5/2004 | McEwen et al. |
| 6,814,079 B2 | 11/2004 | Heaton et al. |
| 6,855,135 B2 | 2/2005 | Lockwood et al. |
| 7,214,202 B1 | 5/2007 | Vogel et al. |
| 2001/0000262 A1 | 4/2001 | McEwen et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0138030 A1 | 9/2002 | Cavanagh et al. |
| 2002/0143286 A1 | 10/2002 | Tumey |
| 2003/0061733 A1 | 4/2003 | Karsten |
| 2003/0125649 A1 | 7/2003 | McIntosh et al. |
| 2003/0216672 A1 | 11/2003 | Rastegar et al. |
| 2005/0020955 A1 | 1/2005 | Sanders et al. |
| 2005/0027218 A1 | 2/2005 | Filtvedt et al. |
| 2006/0100556 A1 | 5/2006 | Hargens et al. |
| 2006/0149171 A1 | 7/2006 | Vogel et al. |
| 2006/0189909 A1 | 8/2006 | Hurley et al. |
| 2006/0189910 A1 | 8/2006 | Johnson et al. |
| 2006/0287621 A1 | 12/2006 | Atkinson et al. |
| 2007/0027414 A1 | 2/2007 | Hoffman et al. |
| 2007/0060848 A1 | 3/2007 | Erdmann |
| 2007/0124959 A1 | 6/2007 | Meffan |
| 2007/0167884 A1 | 7/2007 | Mangrum et al. |
| 2007/0185426 A1 | 8/2007 | Ambrosio et al. |
| 2007/0265585 A1 | 11/2007 | Joshi et al. |
| 2007/0265586 A1 | 11/2007 | Joshi et al. |
| 2008/0047164 A1 | 2/2008 | Vindriis |
| 2008/0066343 A1 | 3/2008 | Sanabria-Hernandez |
| 2008/0071234 A1 | 3/2008 | Kelch et al. |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| DE | 10 2004 055 702 B3 | 11/2005 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| EP | 1 872 763 A1 | 1/2008 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| GB | 2 415 908 A | 1/2006 |
| JP | 4129536 | 4/1992 |
| SG | 71559 | 4/2002 |
| WO | WO 80/02182 | 10/1980 |
| WO | WO 87/04626 | 8/1987 |
| WO | WO 88/01499 A1 | 3/1988 |
| WO | WO 90/10424 | 9/1990 |
| WO | WO 93/09727 | 5/1993 |
| WO | WO 94/20041 | 9/1994 |

| | | |
|---|---|---|
| WO | WO 96/05873 | 2/1996 |
| WO | WO 96/06559 A1 | 3/1996 |
| WO | WO 97/18007 | 5/1997 |
| WO | WO 99/13793 | 3/1999 |
| WO | WO 00/64394 A1 | 11/2000 |
| WO | WO 01/89431 A1 | 11/2001 |
| WO | WO 03/057307 A1 | 7/2003 |
| WO | WO 03/099188 A1 | 12/2003 |
| WO | WO 2005/123170 A1 | 12/2005 |
| WO | WO 2007/092397 A2 | 8/2007 |
| WO | WO 2008/036361 A2 | 3/2008 |
| WO | WO 2008/057600 A2 | 5/2008 |
| WO | WO 2008/100440 A1 | 8/2008 |
| WO | WO 2008/100446 A2 | 8/2008 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.
G. Živadinović, V. Đukić, Ž. Maksimović, Đ.. Radak, and P. Peška, "Vacuum Therapy in the Treatment of Peripheral Blood Vessels," *Timok Medical Journal* 11 (1986), pp. 161-164.
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).
M. Schein, R. Saadia, J.R. Jamieson, and G.A.G. Decker, "The 'Sandwich Technique' in the Management of the Open Abdomen," *British Journal of Surgery* 73 (1986), pp. 369-370.
D.E. Tribble, An Improved Sump Drain-Irrigation Device of Simple Construction, *Archives of Surgery* 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax, "*Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
European Search Report date mailed Apr. 6, 2011 for European Patent Application No. 11153970.6.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A, Solovev, Dissertation Abstract, Treatment and Prevention of Suture Failures after Gastric Resection (S.M. Kirov Gorky State Medical Institute, Gorky, U.S.S.R. 1988) ("Solovev Abstract").
International Search Report and Written Opinion date mailed Jul. 23, 2009 for International PCT Application No. PCT/US2009/037076.
V.A.C.® Therapy Clinical Guidelines: A Reference Source for Clinicians (Jul. 2007)—http://www.kci1.com/Clinical_Guidelines_VAC.pdf, pp. 1-88.
V.A.C.® Therapy Clinical Guidelines: A Reference Source for Clinicians (Jul. 2007)—http://www.kci1.com/Clinical_Guidelines_VAC.pdf, p. 25.

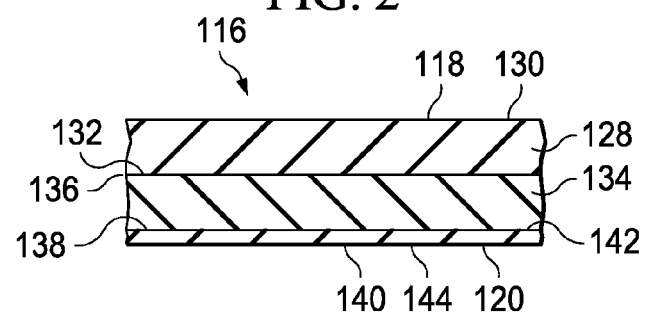
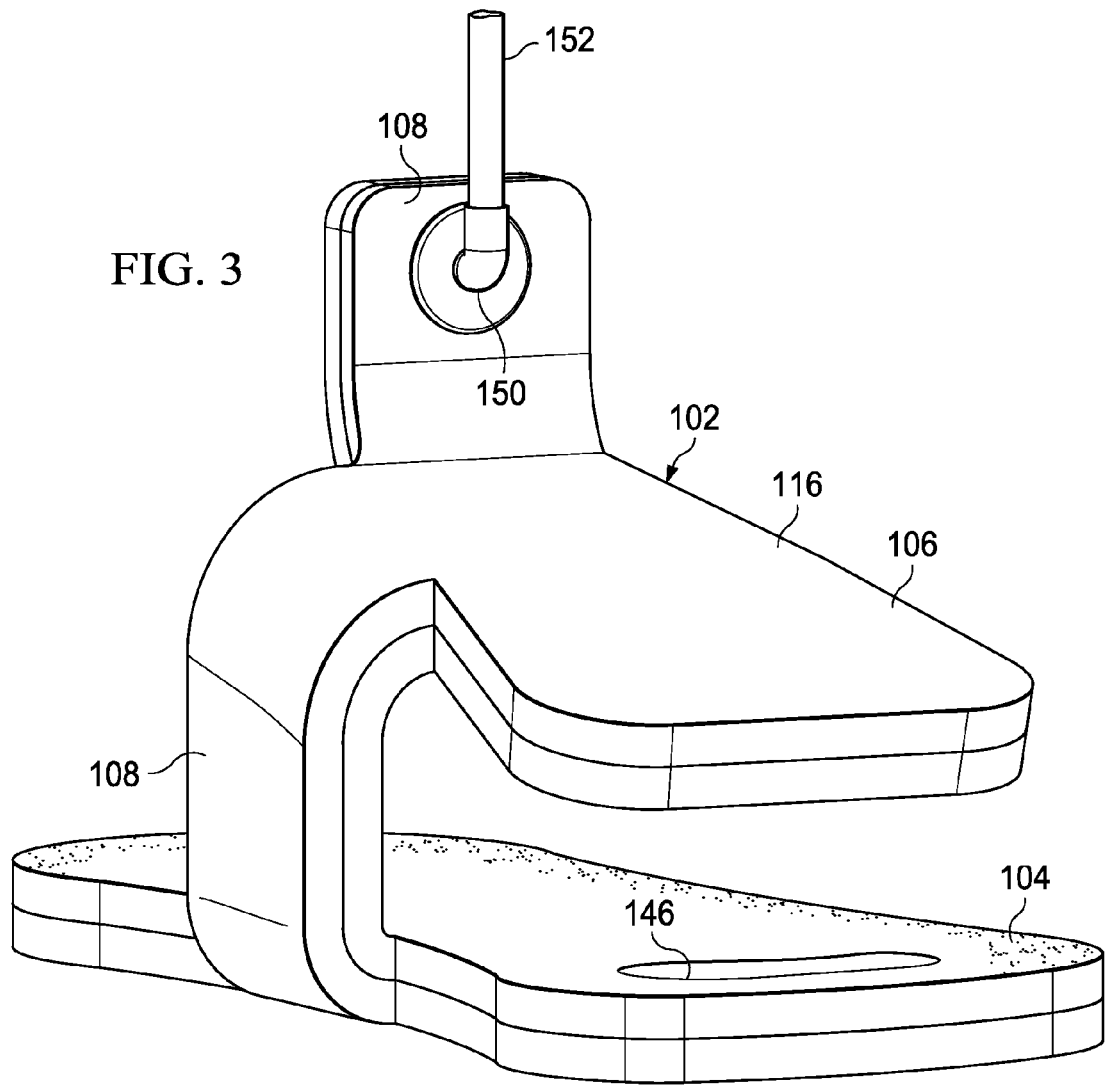

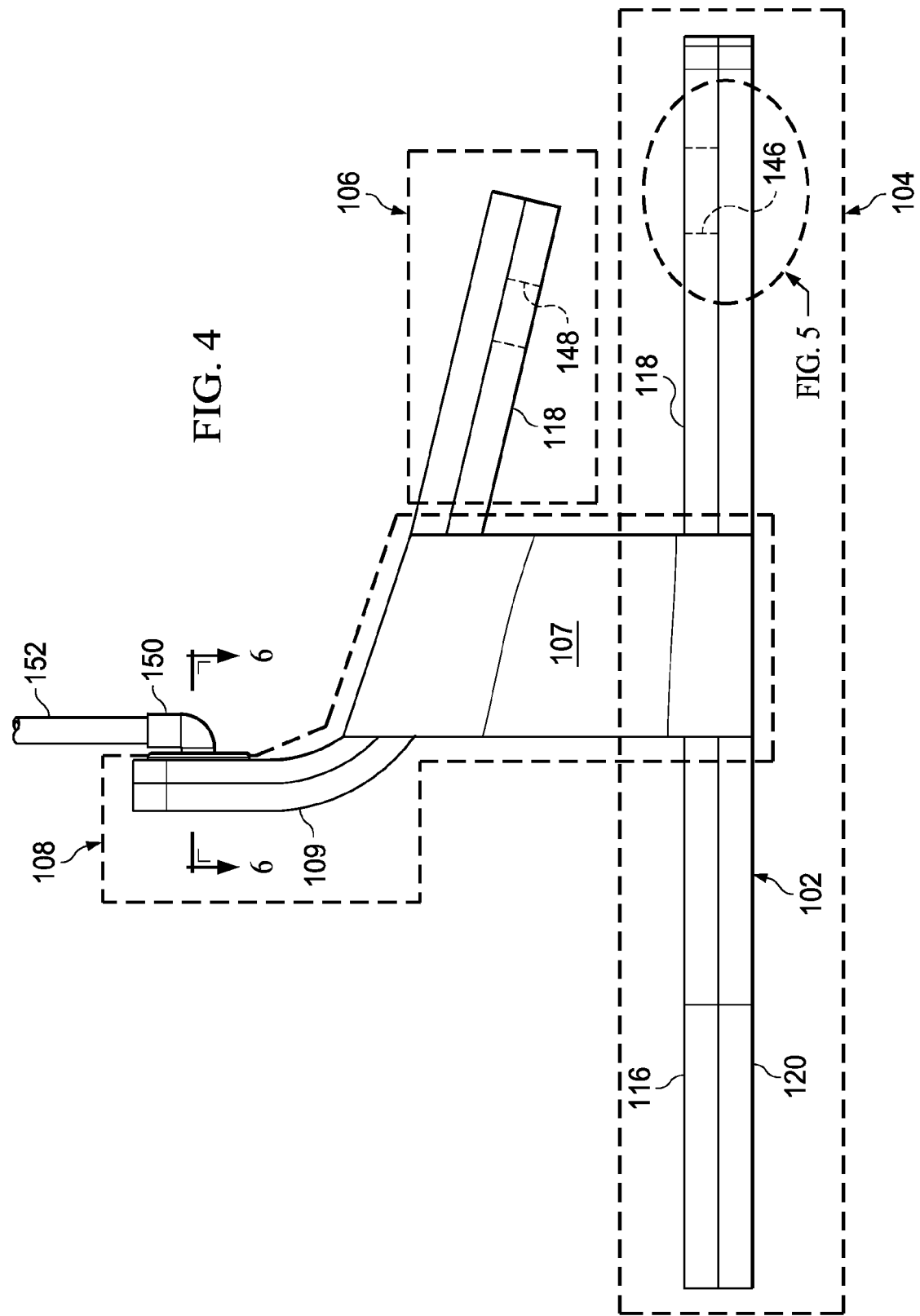

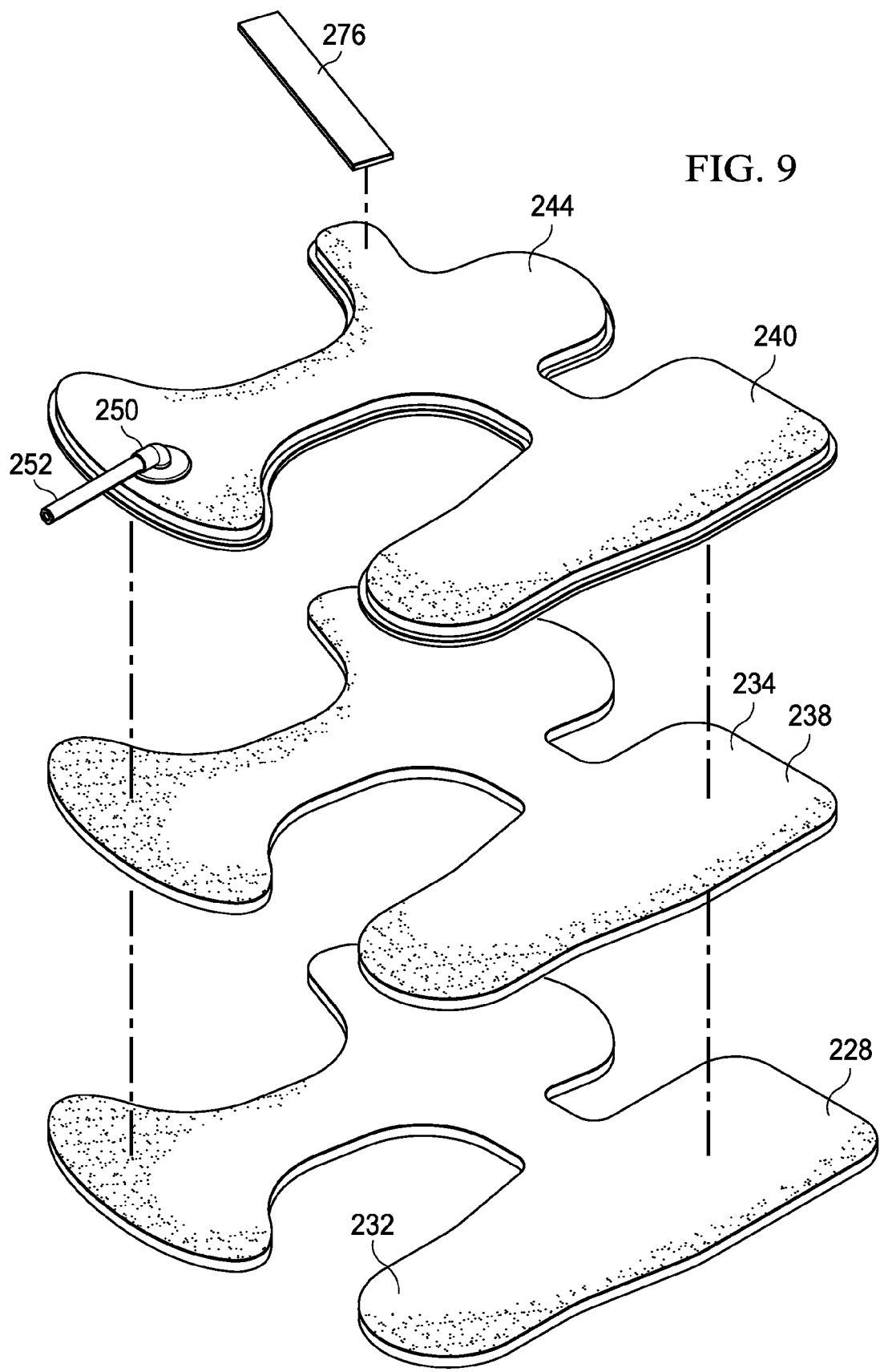

OFFLOADING AND REDUCED-PRESSURE TREATMENT SYSTEMS AND METHODS

RELATED APPLICATIONS

The present invention claims the benefit, under 35 USC §119(e), of the filing of U.S. Provisional Patent Application Ser. No. 61/036,433, filed Mar. 13, 2008, entitled, "System and Method for Applying Reduced Pressure to a Tissue Site on a Foot," which is incorporated herein by reference for all purposes.

BACKGROUND

The present invention relates generally to medical treatment systems and, more particularly, to offloading and reduced-pressure treatment systems, devices, and methods.

It is necessary at times to manage medical problems on a patient's foot or other extremity. Many wounds, or abnormal tissue sites, occur on a patient's foot. For example, diabetics frequently develop neuropathic foot conditions, such as ulcers. Treating the various conditions on extremities, and particularly on the foot, can present many challenges. The treatment may require accommodation, relief of pressure and shear forces, and shock absorption. Devices are often used for such purposes. For example, a total-contact cast, which is made by total-contact casting (TCC), may be used to provide decreased plantar pressures by increasing the weight bearing on the entire lower leg. Numerous other devices may be used also, such as orthotic dynamic system splints, neuropathic walkers, total-contact ankle-foot orthosis, healing sandals, etc. Often the devices involve limited access to the wound or tissue site.

SUMMARY

Problems with existing medical treatment devices and systems for use on extremities are addressed by the systems, devices, and methods of the illustrative embodiments described herein. According to an illustrative embodiment, an offloading and reduced-pressure treatment system includes an offloading and reduced-pressure treatment device, which has a plantar member formed from an offloading manifold material. The offloading manifold material includes a support layer, a pressure-transmitting layer and a second barrier layer. The offloading and reduced-pressure treatment system further includes a reduced-pressure interface fluidly coupled to the pressure-transmitting layer of the plantar member, a reduced-pressure source, and a reduced-pressure delivery conduit fluidly coupled to the reduced-pressure source and to the offloading and reduced-pressure treatment device.

According another illustrative embodiment, an offloading and reduced-pressure treatment device includes a plantar member formed from an offloading manifold material. The offloading manifold material includes a support layer, which has a first surface and a second surface, and a pressure-transmitting layer, which has a first surface and a second surface. The first surface of the pressure-transmitting member is coupled to the second surface of the support layer. The offloading manifold material also includes a second barrier layer, which has a first surface and a second surface. The first surface of the first barrier layer is coupled to the second surface of the pressure-transmitting layer. The offloading and reduced-pressure treatment device further includes a reduced-pressure interface fluidly coupled to the pressure-transmitting layer of the plantar member. The offloading and reduced-pressure treatment device may also have a dorsal member.

According to another illustrative embodiment, an offloading and reduced-pressure treatment device includes a plantar member, which is formed from an offloading manifold material. The offloading manifold material includes a support layer, a pressure-transmitting layer, and a second barrier layer. The offloading and reduced-pressure treatment device further includes a reduced-pressure interface fluidly coupled to the pressure-transmitting layer of the plantar member. The support layer and pressure transmitting layer may be a single layer that is formed with a small-pore ($\leqq 40$ pores per centimeter) open-cell foam that is coated with a non-breathable material.

According another illustrative embodiment, a method of manufacturing an offloading and reduced-pressure treatment device includes the steps of providing a sheet of offloading manifold material and cutting the sheet to form the offloading and reduced-pressure treatment device.

According to another illustrative embodiment, a method for treating a plantar wound on a patient's foot includes the step of providing an offloading and reduced-pressure treatment device formed of an offloading manifold material and having a plantar member. The method of treating a plantar wound on a patient's foot further includes removing a portion of the offloading manifold material to form a first void proximate the plantar wound of the patient; disposing a first treatment manifold in the first void; and delivering reduced pressure to the first void via the pressure-transmitting layer.

According another illustrative embodiment, a method for treating a plantar wound and a dorsal wound on a patient's foot including the step of providing an offloading and reduced-pressure treatment device formed of an offloading manifold material. The offloading and reduced-pressure treatment device has a plantar member and a dorsal member. The method for treating a plantar wound and a dorsal wound further includes removing a portion of the offloading manifold material to form a first void proximate the plantar wound of the patient; disposing a first treatment manifold in the first void; removing another portion of the offloading manifold material to form a second void proximate the dorsal wound of the patient; disposing a second treatment manifold in the second void; and delivering reduced pressure to the first void and second void via the pressure-transmitting layer.

Other objects, features, and advantages of the illustrative embodiments will become apparent with reference to the drawings and detailed description that follow.

BRIEF DESCRIPTION OF THE DRAWINGS

To provide a more complete understanding of the illustrative embodiments and certain of its features and advantages, reference is now made to the following description taken in conjunction with the accompanying drawings, in which:

FIG. 2 is a cross sectional view of a portion of an offloading manifold of the offloading and reduced-pressure treatment system of FIG. 1;

FIG. 3 a schematic, perspective view of the illustrative embodiment of the offloading and reduced-pressure treatment device of the offloading and reduced-pressure treatment system of FIG. 1;

FIG. 4 is a schematic, elevational view of the offloading and reduced-pressure treatment device of the offloading and reduced-pressure treatment system of FIG. 1;

FIG. 9 is a schematic, exploded, perspective view of the illustrative embodiment of the offloading and reduced-pressure treatment device of FIGS. 8A and 8B.

DETAILED DESCRIPTION OF ILLUSTRATIVE EMBODIMENTS

Figure 1:
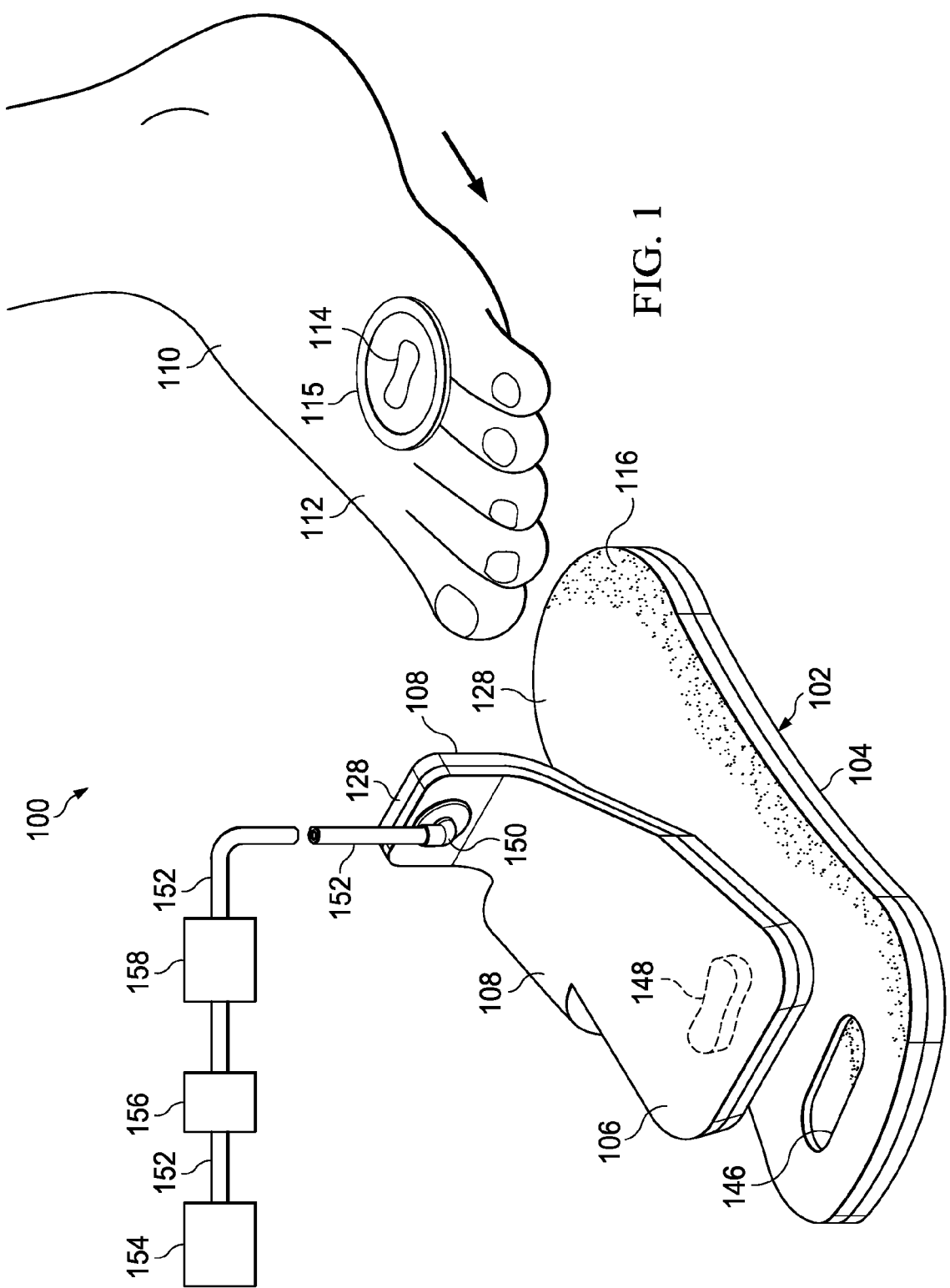
FIG. 1 is a schematic, perspective view, with a portion shown as a block diagram, of an illustrative embodiment of an offloading and reduced-pressure treatment system.

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The systems, methods, and devices herein facilitate offloading and reduced-pressure treatment of tissue, e.g., a wound, on an extremity such as foot. Concerning the latter modality of treatment, clinical studies and practice have shown that providing reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Unless otherwise indicated, as used herein, "or" does not require mutual exclusivity.

Referring to FIG. 1-6, an illustrative embodiment an offloading and reduced-pressure treatment system 100 is presented. The offloading and reduced-pressure treatment system 100 includes an offloading and reduced-pressure treatment device 102, which has a plantar member 104 and may have a dorsal member 106 and a bridge member 108. The bridge member 108 may have a central bridge portion 107 and an interface portion 109. The plantar member 104 is operable to receive a plantar region of a patient's foot 110, which may have a plantar wound 111 (see FIG. 5), such as an ulcer. The dorsal member 106 may be included as part of the offloading and reduced-pressure treatment device 102 and is operable to receive a dorsal region 112 of the patient's foot 110, which may have a dorsal wound 114. The plantar member 104, dorsal member 106, and bridge member 108 are formed from an offloading manifold material 116.

Referring to FIG. 2, a cross sectional view of a portion of the offloading manifold material 116 is presented. The offloading manifold material 116 has a first, tissue-facing surface 118 and a second surface 120. Beginning with the first, tissue-facing surface 118 of the offloading manifold material 116, the offloading manifold material 116 has a support layer 128, which has a first, tissue-facing surface 130 and a second surface 132. The offloading manifold material 116 also includes a pressure-transmitting layer 134, which has a first, tissue-facing surface 136 and a second surface 138. The first, tissue-facing surface 136 of the pressure-transmitting layer 134 is coupled to the second surface 132 of the support layer 128. The offloading manifold material 116 also includes a first barrier layer 140, which has a first, tissue-facing surface 142 and a second surface 144. The first, tissue-facing surface 142 of the first barrier layer 140 is coupled to the second surface 138 of the pressure-transmitting layer 134. The pressure-transmitting layer 134 may be sized smaller than the support layer 128 and the first barrier layer 140 so that the pressure-transmitting layer 134 may be contained fully between the support layer 128 and the first barrier layer 140.

As used herein, the term "coupled" includes coupling via a separate object and includes direct coupling. The term "coupled" also encompasses two or more components that are continuous with one another by virtue of each of the components being formed from the same piece of material. Also, the term "coupled" may include chemical, such as via a chemical bond, mechanical, thermal, or electrical coupling. Fluid coupling means that fluid is in communication between the designated parts or locations. The overall thickness of the three layers (support layer 128, pressure-transmitting layer 134, and first barrier layer 140) is preferably in the range of 4 mm to 15 mm and more preferably in the range of 6 mm to 10 mm.

The first barrier layer 140 provides protection and helps seal the offloading and reduced-pressure treatment device 102. The first barrier layer 140 may be formed from various materials, such a flexible, non-breathable material, fluid-impermeable or fluid-resistant material. A non-limiting example of a suitable non-breathable material is a polyurethane and fabric material and a more specific non-limiting example is a polyurethane transfer coating on a warp knitted fabric (42% polyurethane and 58% fabric). The first barrier layer 140 may also be puncture resistant.

The support layer 128 provides a support structure and allows offloading of physical pressure. As such, the support layer 128 removes pressure from around a wound being treated. The support layer 128 may be able to cushion, absorb shock, relieve pressure, or may even control abnormal foot and leg motion. As one illustrative example, the support layer 128 may be formed from a closed-cell foam. The closed-cell foam may be formed from a cellular polyethylene foam.

The pressure-transmitting layer 134 allows reduced pressure to be transmitted via the layer and to transmit any fluids, e.g., exudates. One suitable material for the pressure-transmitting layer 134 is a flexible, open-cell foam, e.g., a GranuFoam® material, which is available from Kinetic Concepts, Inc. of San Antonio, Tex.

In an alternative embodiment, the support layer 128 and pressure-transmitting layer 134 may be a single layer that is formed with a small-pore (40 pores per centimeter or smaller) open-cell foam that is coated with a non-breathable material that also provides some offloading strength. For example, the small-pore foam may be covered with a vinyl material.

Referring again to FIGS. 1-6, a portion of the support layer 128 may be cut and removed to form a first void 146, or plantar void, that aligns with a plantar wound 111 and that is larger than the plantar wound 111. In this way, the plantar member 104 provides an offloading function proximate the plantar wound 111. In a similar fashion, another portion of the support layer 128 is cut and removed to form a second void 148, or dorsal void, on a portion of the dorsal member 106. Again, the second void 148 helps offload pressure from a dorsal wound on the patient's foot 110 or to protect and provide space for treatment. A sealing member 115, e.g., a ring of adhesive material such as a hydrocolloid ring, may be used to form a pneumatic seal between the offloading and reduced-pressure treatment device 102 and the patient's skin near the dorsal wound 114. Another sealing member 162 analogous to the sealing member 115 may be placed around the plantar wound 111. Only two wounds, the plantar wound 111 and the dorsal wound 114, have been shown, but additional portions of the offloading and reduced-pressure treatment device 102 may be removed to form additional voids for treating additional wounds.

A reduced-pressure interface 150 may be located at any location on the offloading and reduced-pressure treatment device 102 and fluidly coupled to, i.e., is in fluid communication with, the pressure-transmitting layer 134 of the offloading manifold material 116. If an embodiment only includes the plantar member 104, then the reduced-pressure interface 150 is coupled to a portion of the plantar member 104. If a dorsal member 106 is included in the embodiment, the reduced-pressure interface 150 may be coupled to the dorsal member 106 or the plantar member 104. In the embodiment shown in FIG. 1, the reduced-pressure interface 150 is coupled to a portion of the bridge member 108. In coupling the reduced-pressure interface 150, an aperture is formed through the first barrier layer 140 and the reduced-pressure interface 150 is brought into fluid communication with the pressure-transmitting layer 134. The bridge member 108 provides a convenient location for the reduced-pressure interface 150 and is fluidly coupled to the plantar member 104. If the dorsal member 106 is included, the bridge member 108 helps couple the dorsal member 106 and the plantar member 104 and fluidly couples the reduced-pressure interface 150 to the pressure-transmitting layer 134 of the dorsal member 106.

A reduced-pressure delivery conduit 152 is fluidly coupled to the reduced-pressure interface 150 and to a reduced-pressure source 154. The reduced-pressure interface 150 may be a port, such as a TRAC Pad® interface or a SensaT.R.A.C.™ pad interface from Kinetic Concepts, Inc. of San Antonio, Tex. The reduced-pressure source 154 may be any device or means for supplying reduced pressure, such as a vacuum pump, manually-actuated pump, or a wall suction source. While the amount and nature of reduced pressure applied to a tissue site, e.g., wound, will vary according to the application, the reduced pressure will typically be between −5 mm Hg and −500 mm Hg and more typically between −150 mm Hg and −300 mm Hg.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure. Consistent with the use herein, an increase in reduced pressure or vacuum pressure typically refers to a relative reduction in absolute pressure. In one illustrative embodiment, a V.A.C.® Therapy Unit by Kinetic Concepts, Inc. of San Antonio may be used as the reduced-pressure source 154.

Depending on the application, a plurality of devices may be fluidly coupled to the reduced-pressure delivery conduit 152. For example, a fluid canister 156 or a representative device 158 may be included. The representative device 158 may be another fluid reservoir or canister to hold exudates and other fluids removed. Other examples of the representative device 158 that may be included on the reduced-pressure delivery conduit 152 include the following non-limiting examples: a pressure-feedback device, a volume detection system, a blood detection system, an infection detection system, a flow monitoring system, a temperature monitoring system, a filter, etc. Some of these devices may be formed integral to a reduced-pressure source 154.

Figure 5:
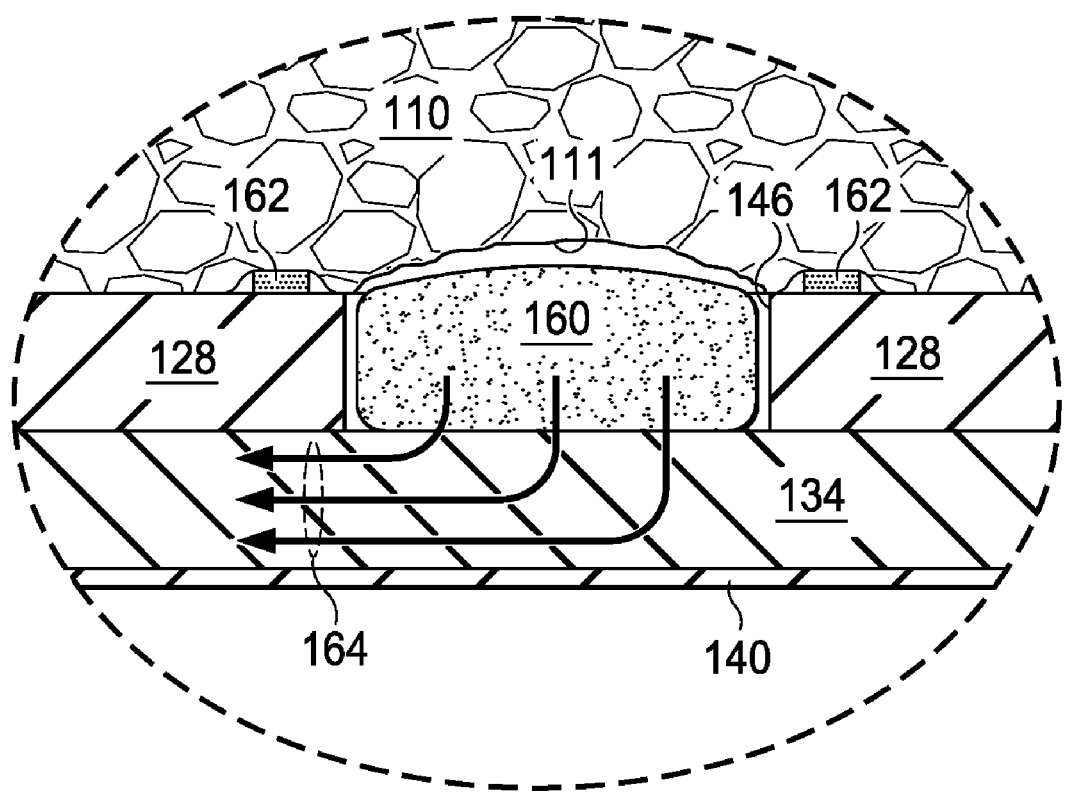
FIG. 5 is a portion of a longitudinal cross section of a plantar member of the offloading and reduced-pressure treatment device of the offloading and reduced-pressure treatment system of FIG. 1.
Figure 6:
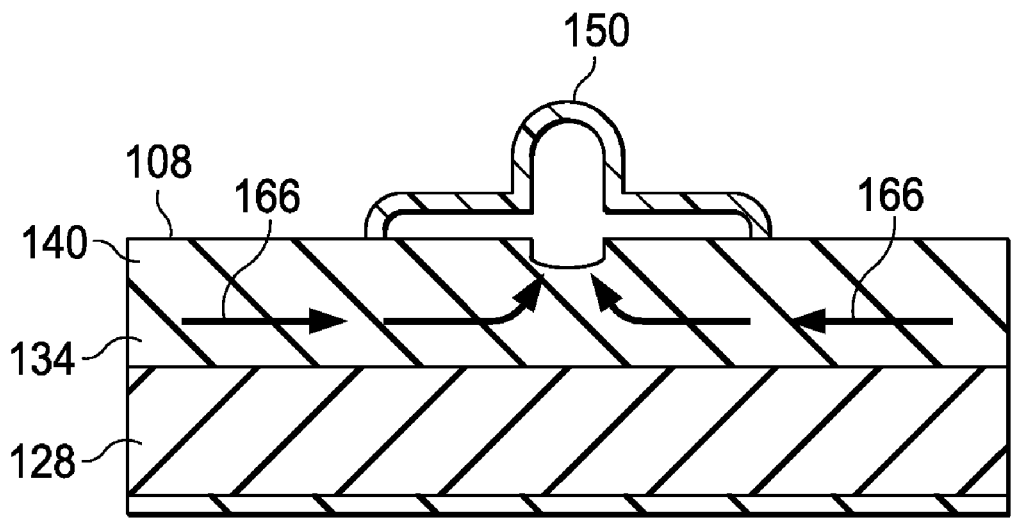
FIG. 6 is a cross-sectional view of the offloading and reduced-pressure treatment device of FIG. 4 taken along line 6-6.

Referring now primarily to FIGS. 1 and 5, the application of the offloading and reduced-pressure treatment device 102 to the plantar wound 111 will be described. The healthcare provider removes a first portion of the support layer 128 at the location that corresponds or aligns with the plantar wound 111 when the foot 110 is placed onto the plantar member 104. The support layer 128 may be cut and removed with the assistance of a tool, such as a scalpel. As the first portion is removed, the first void 146 is formed.

A first treatment manifold 160, or plantar treatment manifold, is placed into the first void. The term "manifold" as used herein generally refers to a substance or structure that is provided to assist in applying reduced pressure to, delivering fluids to, or removing fluids from a tissue site. The manifold typically includes a plurality of flow channels or pathways that are interconnected to improve distribution of fluids provided to and removed from the tissue site or wound, e.g., plantar wound 111, around the first treatment manifold 160. The first treatment manifold 160 may be a biocompatible material that is capable of being placed in contact with the tissue site or wound, e.g., plantar wound 111, and distributing reduced pressure to the tissue site or wound, e.g., plantar wound 111. Examples of treatment manifolds may include, for example, without limitation, devices that have structural elements arranged to form flow channels, such as, for example, cellular foam, open-cell foam, porous tissue collections, liquids, gels, and foams that include, or cure to include, flow channels. The first treatment manifold 160 may be porous and may be made from foam, gauze, felted mat, or any other material suited to a particular biological application. In one embodiment, the treatment manifold is a porous foam and includes a plurality of interconnected cells or pores that act as flow channels. The porous foam may be a polyurethane, open-cell, reticulated foam, such as a GranuFoam® material manufactured by Kinetic Concepts, Incorporated of San Antonio, Tex. In some situations, the treatment manifold, e.g., first treatment manifold 160, may also be used to distribute fluids, such as medications, antibacterials, growth factors, and various solutions to the tissue site or wound, e.g., plantar wound 111. Other layers may be included in or on the treatment manifold, such as absorptive materials, wicking materials, hydrophobic materials, and hydrophilic materials.

The first treatment manifold 160 may be slightly taller than the height of the first void 146 (for the orientation shown in FIG. 5) to provide contact with the plantar wound 111. The sealing member 162, which may be an adhesive, such as a hydrocolloid, is applied to the plantar region of the foot 110 proximate the plantar wound 111, and the foot 110 is then placed on the plantar member 104. The plantar wound 111 is aligned with the first void 146 of the offloading and reduced-pressure treatment device 102 and the foot 110 is placed on the plantar member 104. The sealing member 162 forms a pneumatic seal around the plantar wound 111 over the first void 146, which contains the first treatment manifold 160. With respect to the dorsal member 106, an analogous procedure is done to create the second void 148 in the dorsal member 106 and a second treatment manifold, or dorsal treatment manifold, is placed in the second void 148. The offloading and reduced-pressure treatment device 102, which has been placed on the foot 110, may then be placed in a cast shoe, sandal, or over size shoe.

Reduced pressure is supplied to the reduced-pressure interface 150. Reduced pressure is transmitted in the pressure-transmitting layer 134 to the first void 146 and the first treatment manifold 160 and the second void 148 and the second treatment manifold. As suggested by arrows 164 in FIG. 5, reduced pressure pulls any fluids from the plantar wound 111 into the first treatment manifold 160 and into the pressure-transmitting layer 134, and as suggested by arrows 166 in FIG. 6, the fluids are pulled into the reduced-pressure interface 150. The fluids delivered to the reduced-pressure interface 150 may be delivered by the reduced-pressure delivery conduit 152 to the fluid canister 156.

Figure 7A:
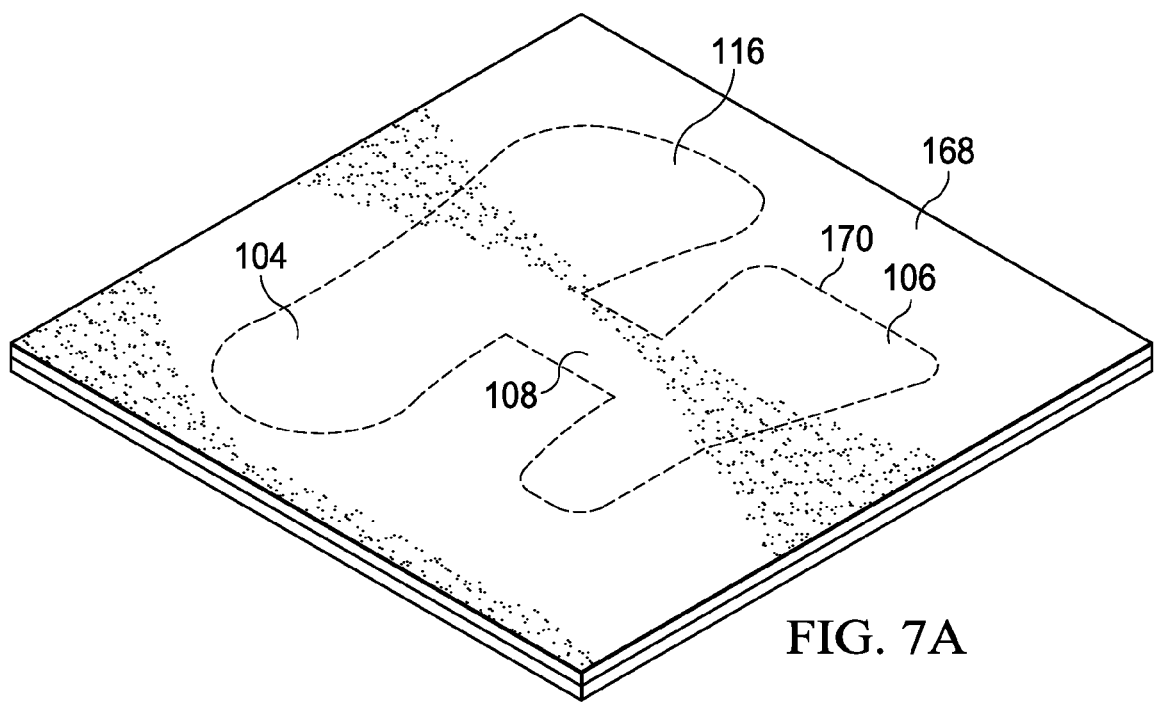
FIG. 7A is a schematic, perspective view of a sheet of offloading manifold material.
Figure 7B:
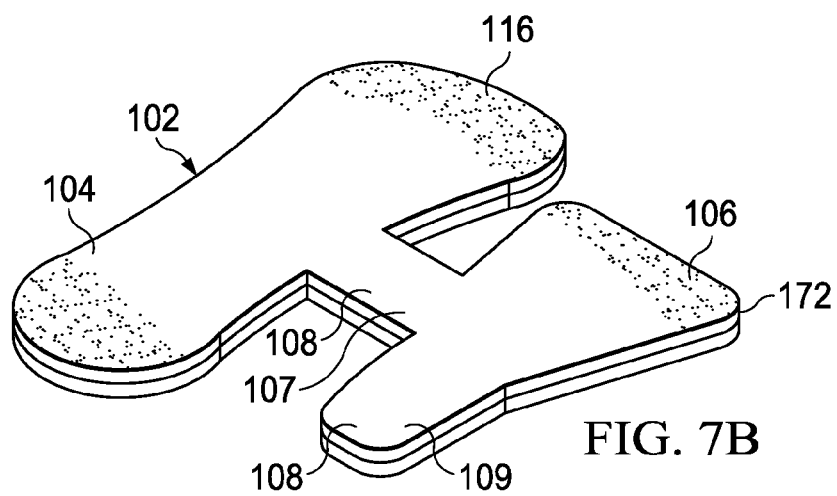
FIG. 7B is a schematic, perspective view of an offloading and reduced-pressure treatment device after cutting and before folding.

Referring now to FIGS. 7A and 7B, an illustrative process for manufacturing the offloading and reduced-pressure treatment device 102 is presented. A sheet 168 of offloading manifold material 116 may be provided. For example a 30.5 cm×30.5 cm sheet of offloading manifold material 116 may be provided that is used to form the offloading and reduced-pressure treatment device 102 for use on a foot or other extremity. A pattern 170 may be marked and cut that corresponds to the patient's foot size. In the current embodiment, the plantar member 104 is sized based on a particular sizing for a patient and then the pattern 170 produced. The pattern 170 is cut to form an unfolded offloading and reduced-pressure treatment device 102 as shown in FIG. 7B. Edges 172 of the cut offloading and reduced-pressure treatment device 102 may be covered with a flexible adhesive tape or sprayed with a quick-drying sealant. The unfolded offloading and reduced-pressure treatment device 102 is then folded to form the device into the position shown in FIGS. 1, 3, and 4.

Figure 8A:
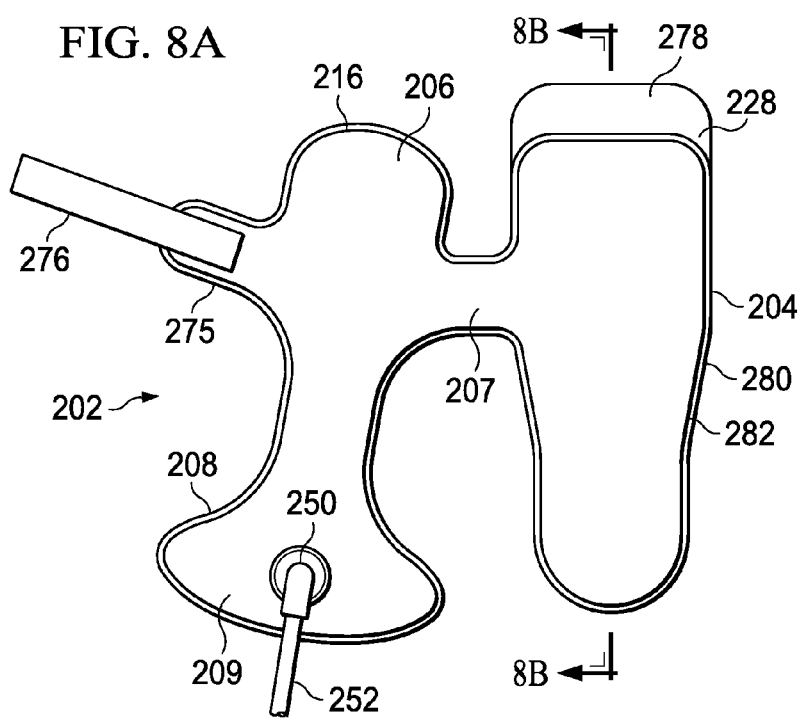
FIG. 8A is a schematic, plan view of an illustrative embodiment of an offloading and reduced-pressure treatment device.
Figure 8B:
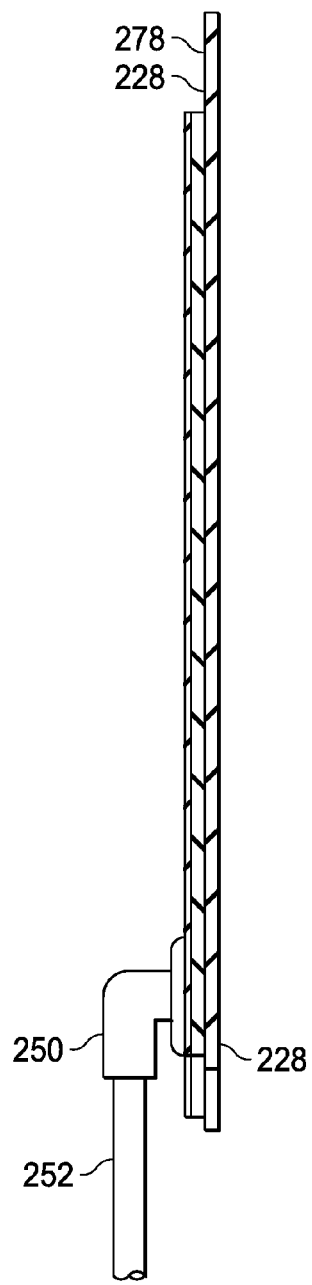
FIG. 8B is an enlarged, cross-sectional view of the illustrative embodiment of an offloading and reduced-pressure treatment device of FIG. 8A taken along line 8B-8B.

Referring now to FIGS. 8A, 8B, and 9 another illustrative embodiment of an offloading and reduced-pressure treatment device 202 is presented. The offloading and reduced-pressure treatment device 202 is analogous to the offloading and reduced-pressure treatment device 102 of FIGS. 1-7 and analogous or same parts are indicated by indexing the references numerals by 100. The offloading and reduced-pressure treatment device 202 has a plantar member 204 and may have a dorsal member 206 and a bridge member 208. The bridge member 208 may have a central bridge portion 207 and an interface portion 209. The plantar member 204 is operable to receive a plantar region of a patient's foot, which may have a plantar wound. The dorsal member 206 may be included as part of the offloading and reduced-pressure treatment device 202 and is operable to receive a dorsal region of the patient's foot, which may have a dorsal wound. The plantar member 204, dorsal member 206, and bridge member 208 are formed from an offloading manifold material 216.

The offloading manifold material 216 has a support layer 228, pressure-transmitting layer 234, and a first barrier layer 240. The support layer 228 has a first, tissue-facing surface and a second surface 232. The pressure-transmitting layer 234 has a first, tissue-facing surface and a second surface 238. The first barrier layer 240 has a first, tissue-facing surface and a second surface 244.

A reduced-pressure interface 250 may be applied anywhere, but preferably on the interface portion 209 of the bridge member 208. The reduced-pressure interface 250 is fluidly coupled to a reduced-pressure delivery conduit 252 which is fluidly coupled to a reduced-pressure source.

The offloading and reduced-pressure treatment device 202 includes an extension member 275 that extends from the bridge member 208. The extension member 275 helps to secure the offloading and reduced-pressure treatment device 202 in position during use. A securing strip 276 is attached to the extension member 275 and releasably attaches to a portion of the plantar member 204. The securing strip 276 may be a piece of drape material with an adhesive or a hook-and-loop member, etc.

Referring to FIGS. 8A and 8B, an additional feature of the offloading and reduced-pressure treatment device 202 may be seen. In this embodiment, an adjustment portion 278 of the support layer 228 may be seen. In use, the adjustment portion 278 is placed under the patient's phalanges or the metatarsal bones. The adjustment portion 278 may be cut to accommodate different size feet or shoes as necessary. The adjustment portion 278 allows the offloading and reduced-pressure treatment device 202 to be manufactured with a set size and then be customized within a certain range for a particular user.

Figure 10:
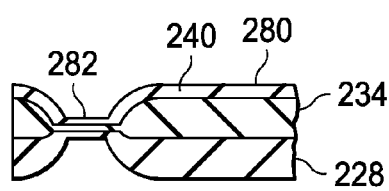
FIG. 10 is a cross section of a portion of the offloading manifold for use with the offloading and reduced-pressure treatment device of FIG. 8A.

Referring to FIG. 8A and FIG. 10, a perimeter 280 of the offloading and reduced-pressure treatment device 202 has a seal 282. The seal 282 may be formed in numerous ways, such as glue, glue and pressing with a lip on a jig to apply force (see FIG. 10), bonding, welding, drape tape, cements, etc. The seal 282 provides a pneumatic seal to the edge of the pressure-transmitting layer 234 and couples the support layer 228, pressure-transmitting layer 234, and first barrier layer 240.

Although the present invention and its advantages have been disclosed in the context of certain illustrative, non-limiting embodiments, it should be understood that various changes, substitutions, permutations, and alterations can be made without departing from the scope of the invention as defined by the appended claims.

What is claimed:

1. An offloading and reduced-pressure treatment system comprising:
    an offloading and reduced-pressure treatment device, wherein the offloading and reduced-pressure treatment device comprises:
        a plantar member formed from an offloading manifold material;
        wherein the offloading manifold material comprises:
            a support layer having a first, tissue-facing surface and a second surface,
            a pressure-transmitting layer having a first, tissue-facing surface and a second surface, the first, tissue-facing surface of the pressure-transmitting layer coupled to the second surface of the support layer, and a first barrier layer having a first, tissue-facing surface and a second surface, the first, tissue-facing surface of the first barrier layer coupled to the second surface of the pressure-transmitting layer;
a reduced-pressure interface fluidly coupled to the pressure-transmitting layer of the plantar member;
a reduced-pressure source; and
a reduced-pressure delivery conduit fluidly coupled to the reduced-pressure source and to the reduced-pressure interface.

2. The offloading and reduced-pressure treatment system of claim 1 wherein the pressure transmitting layer is encapsulated by the support layer, the first barrier layer, and a seal.

3. The offloading and reduced-pressure treatment system of claim 1 wherein the offloading and reduced-pressure treatment device further comprises a dorsal member formed of the offloading manifold material wherein the pressure-transmitting layer of the dorsal member is fluidly coupled to the pressure-transmitting layer of the plantar member.

4. The offloading and reduced-pressure treatment system of claim 1 wherein the offloading and reduced-pressure treatment device further comprises a bridge member formed from the offloading manifold material and wherein the pressure-transmitting layer of the bridge member is fluidly coupled to the pressure-transmitting layer of the plantar member and wherein the reduced-pressure interface is coupled to the bridge member.

5. The offloading and reduced-pressure treatment system of claim 1 wherein the offloading and reduced-pressure treatment device further comprises:
a dorsal member formed from the offloading manifold material and wherein the pressure-transmitting layer of the dorsal member is fluidly coupled to the pressure-transmitting layer of the plantar member; and
a bridge member formed from the offloading manifold material and wherein the pressure-transmitting layer of the bridge member is fluidly coupled to the pressure-transmitting layer of the plantar member and wherein the reduced-pressure interface is coupled to the bridge member.

6. The offloading and reduced-pressure treatment system of claim 1 wherein the offloading manifold material comprises:
the pressure-transmitting layer comprises an open-cell foam material, and
the support layer comprises a closed-cell foam material.

7. The offloading and reduced-pressure treatment system of claim 1, wherein a portion of the support layer of the plantar member is removable to form a first void and the pressure-transmitting layer of the plantar member is operable to transfer reduced pressure to the first void.

8. The offloading and reduced-pressure treatment system of claim 5 wherein a portion of the support layer of the plantar member is removable to form a first void, the pressure-transmitting layer of the plantar member is operable to transfer reduced pressure to the first void, a portion of the support layer of the dorsal member is removable to form a second void, and the pressure-transmitting layer of the dorsal member is operable to transfer reduced pressure to the second void.

9. An offloading and reduced-pressure treatment device comprising:
a plantar member, the plantar member formed from an offloading manifold material;
wherein the offloading manifold material comprises:
a support layer having a first surface and a second surface,
a pressure-transmitting layer having a first surface and a second surface, the first surface of the pressure-transmitting layer coupled to the second surface of the support layer, and
a first barrier layer having a first surface and a second surface, the first surface of the first barrier layer coupled to the second surface of the pressure-transmitting layer; and
a reduced-pressure interface fluidly coupled to the pressure-transmitting layer of the plantar member.

10. The offloading and reduced-pressure treatment device of claim 9 wherein the pressure transmitting layer is encapsulated by the support layer, the first barrier layer, and a seal.

11. The offloading and reduced-pressure treatment device of claim 9 further comprising a dorsal member formed from the offloading manifold material and wherein the pressure-transmitting layer of the dorsal member is fluidly coupled to the pressure-transmitting layer of the plantar member.

12. The offloading and reduced-pressure treatment device of claim 9 further comprising a bridge member formed from the offloading manifold material wherein the pressure-transmitting layer of the bridge member is fluidly coupled to the pressure-transmitting layer of the plantar member and wherein the reduced-pressure interface is coupled to the bridge member.

13. The offloading and reduced-pressure treatment device of claim 9 further comprising:
a dorsal member formed from the offloading manifold material and wherein the pressure-transmitting layer of the dorsal member is fluidly coupled to the pressure-transmitting layer of the plantar member; and
a bridge member formed from the offloading manifold material, wherein the pressure transmitting layer of the bridge member is fluidly coupled to the pressure-transmitting layer of the plantar member, and wherein the reduced-pressure interface is coupled to the bridge member.

14. The offloading and reduced-pressure treatment device of claim 13 wherein a portion of the support layer of the plantar member is removable to form a first void, the pressure-transmitting layer of the plantar member is operable to transfer reduced pressure to the first void, a portion of the support layer of the dorsal member is removable to form a second void, and the pressure-transmitting layer of the dorsal member is operable to transfer reduced pressure to the second void.

15. The offloading and reduced-pressure treatment device of claim 9 wherein the offloading manifold material comprises:
the pressure-transmitting layer comprises an open-cell foam material, and
the support layer comprises a closed-cell foam material.

16. The offloading and reduced-pressure treatment device of claim 9 wherein a portion of the support layer of the plantar member is removable to form a first void and the pressure-transmitting layer of the plantar member is operable to transfer the reduced pressure to the first void.

17. The offloading and reduced-pressure treatment device of claim 9 wherein the offloading manifold material has a perimeter and wherein the offloading manifold material is sealed by a sealing member proximate the perimeter.

18. The offloading and reduced-pressure treatment device of claim 9 wherein the support layer further comprises an adjustment portion for facilitating adjustment of the size of the offloading and reduced-pressure treatment device.

19. An offloading and reduced-pressure treatment device comprising:
a plantar member, the plantar member formed from an offloading manifold material;
wherein the offloading manifold material comprises: a support layer, a pressure-transmitting layer, and a first barrier layer; and
a reduced-pressure interface fluidly coupled to the pressure-transmitting layer of the plantar member, wherein the support layer and the pressure transmitting layer comprise a single layer that is formed with a small-pore (≦40 pores per centimeter) open-cell foam that forms the pressure-transmitting layer and that is coated with a non-breathable material to form the support layer.

20. The offloading and reduced-pressure treatment device of claim 19 wherein the pressure-transmitting layer is encapsulated by the first-barrier layer and the non-breathable material.

21. A method of manufacturing an offloading and reduced-pressure treatment device, the method comprising:
providing a sheet of offloading manifold material, the offloading manifold material comprising:
a support layer having a first surface and a second surface,
a pressure-transmitting layer adapted to transmit reduced pressure, the pressure-transmitting layer having a first surface and a second surface, the first surface of the pressure-transmitting layer coupled to the second surface of the support layer, and
a first barrier layer having a first surface and a second surface, the first surface of the first barrier layer coupled to the second surface of the pressure-transmitting layer; and
cutting the sheet to form the offloading and reduced-pressure treatment device.

22. The method of manufacturing of claim 21, further comprising the step of folding the sheet to form the offloading and reduced-pressure treatment device.

23. The method of manufacturing of claim 21 wherein:
the pressure-transmitting layer of the offloading manifold material comprises an open-cell foam material, and
the support layer of the offloading manifold material comprises a closed-cell foam material.

24. The method of manufacturing of claim 21 wherein the step of cutting the sheet to form the offloading and reduced-pressure treatment device comprises the step of cutting the sheet to form a plantar member, a bridge member, and a dorsal member.

25. The method of manufacturing of claim 21 wherein the pressure transmitting layer is encapsulated by the support layer, the first barrier layer, and a seal.

26. A method for treating a plantar wound on a patient's foot, the method comprising the steps of:
providing an offloading and reduced-pressure treatment device formed from an offloading manifold material, the offloading and reduced-pressure treatment device having a plantar member, and wherein the offloading manifold material comprises:
a support layer having a first surface and a second surface,
a pressure-transmitting layer having a first surface and a second surface, the first surface of the pressure-transmitting layer coupled to the second surface of the support layer, and
a first barrier layer having a first surface and a second surface, the first surface of the first barrier layer coupled to the second surface of the pressure-transmitting layer;
removing a portion of the support layer to form a first void proximate the plantar wound of the patient;
disposing a first treatment manifold in the first void; and
delivering reduced pressure to the first void via the pressure-transmitting layer.

27. The method for treating a plantar wound on a patient's foot of claim 26 further comprises the step of disposing a first sealing member around the first void, the first sealing member operable to form a pneumatic seal between the support layer and the patient's skin.

28. The method for treating a plantar wound on a patient's foot of claim 26 wherein:
the pressure-transmitting layer of the offloading manifold material comprises an open-cell foam material, and
the support layer of the offloading manifold material comprises a closed-cell foam material.

29. A method for treating a plantar wound and a dorsal wound on a patient's foot, the method comprising the steps of:
providing an offloading and reduced-pressure treatment device formed from an offloading manifold material, the offloading and reduced-pressure treatment device having a plantar member and a dorsal member, and wherein the offloading manifold material comprises:
a support layer having a first surface and a second surface,
a pressure-transmitting layer having a first surface and a second surface, the first surface of the pressure-transmitting layer coupled to the second surface of the support layer, and
a first barrier layer having a first surface and a second surface, the first surface of the first barrier layer coupled to the second surface of the pressure-transmitting layer;
removing a portion of the support layer to form a first void proximate the plantar wound of the patient;
disposing a first treatment manifold in the first void;
removing a portion of the support layer to form a second void proximate the dorsal wound of the patient;
disposing a second treatment manifold in the second void; and
delivering reduced pressure to the first void and the second void via the pressure-transmitting layer.

30. The method for treating a plantar wound and a dorsal wound on a patient's foot of claim 29 further comprises the step of disposing a first sealing member around the first void, the first sealing member operable to form a pneumatic seal between the support layer of the plantar member and the patient's skin; and the step of disposing a second sealing member around the second void, the second sealing member operable to form a pneumatic seal between the support layer of the dorsal member and the patient's skin.

31. The method for treating a plantar wound and a dorsal wound on a patient's foot of claim 30 wherein:
the pressure-transmitting layer of the offloading manifold material comprises an open-cell foam material, and
the support layer of the offloading manifold material comprises a closed-cell foam material.

32. The method for treating a plantar wound and a dorsal wound on a patient's foot of claim 30 wherein:
the pressure-transmitting layer of the offloading manifold material comprises an open-cell foam material,
the support layer of the offloading manifold material comprises a closed-cell foam material, and
the first barrier layer of the offloading manifold material comprises a polyurethane transfer coating on a warp knitted fabric.

* * * * *